(12) United States Patent
Lee

(10) Patent No.: US 8,476,556 B2
(45) Date of Patent: Jul. 2, 2013

(54) GEMSTONE HEATING SYSTEM WITH MAGNET FOR EXPANDING CAPILLARY VESSEL

(76) Inventor: Wonwoo Lee, Seoul (KR)

( * ) Notice: Subject to any disclaimer, the term of this patent is extended or adjusted under 35 U.S.C. 154(b) by 455 days.

(21) Appl. No.: 12/268,568

(22) Filed: Nov. 11, 2008

(65) Prior Publication Data
US 2010/0116804 A1   May 13, 2010

(51) Int. Cl.
   *H05B 1/00*    (2006.01)
   *H05B 3/02*    (2006.01)
   *H05B 11/00*   (2006.01)
(52) U.S. Cl.
   USPC ............................................. 219/201; 219/227
(58) Field of Classification Search
   USPC ........... 219/201, 227, 228, 229, 465.1, 468.2, 219/544, 546, 547, 548, 552, 553; 338/252, 338/311
   See application file for complete search history.

(56) References Cited

U.S. PATENT DOCUMENTS

| | | | | |
|---|---|---|---|---|
| 2,097,455 A * | 11/1937 | Fisher | .............................. | 601/18 |
| 2,779,328 A * | 1/1957 | Grossi | .............................. | 601/18 |
| 4,691,693 A * | 9/1987 | Sato | .............................. | 601/15 |
| 6,187,031 B1 * | 2/2001 | Douglas | .............................. | 607/112 |
| 6,461,377 B1 * | 10/2002 | An | .............................. | 607/96 |
| 6,866,776 B2 * | 3/2005 | Leason et al. | .............................. | 210/201 |
| 6,939,367 B2 * | 9/2005 | Harrison | .............................. | 607/109 |
| 7,169,120 B2 * | 1/2007 | Murdock et al. | .............................. | 601/129 |
| 7,238,162 B2 * | 7/2007 | Dehli | .............................. | 601/16 |
| 7,270,640 B2 * | 9/2007 | Boys | .............................. | 601/78 |
| 2002/0169398 A1 * | 11/2002 | Hancock | .............................. | 601/15 |
| 2009/0254155 A1 * | 10/2009 | Kanarsky et al. | .............................. | 607/89 |

* cited by examiner

*Primary Examiner* — Tu B Hoang
*Assistant Examiner* — Hemant Mathew
(74) *Attorney, Agent, or Firm* — John K. Park; Park Law Firm

(57) ABSTRACT

An aspect of the invention provides a gemstone heating system for expanding capillary vessel. The system comprises a gemstone heating pad, a magnet, a heat conductor, a heating element, and an insulating cover. The gemstone heating pad comprises a front surface, a rear surface, a recess portion provided on a central portion of the rear surface, a enclosing wall portion configured for enclosing the recess portion. The magnet is embedded in the recess portion of the gemstone heating pad. The heat conductor encloses the recess portion of the gemstone heating system. The heating element is disposed in the heating conductor. The insulating cover is configured for insulating the heat conductor and the heating element.

17 Claims, 4 Drawing Sheets

GEMSTONE HEATING SYSTEM WITH MAGNET FOR EXPANDING CAPILLARY VESSEL

BACKGROUND OF THE INVENTION

The present invention relates to a gemstone heating system with magnet for expanding capillary vessel. More particularly, this invention relates to a gemstone heating system for expanding capillary vessel, which applies heat to a portion of skin for relieving medical symptoms including pain of the skin or tissues below the skin.

Blood circulation seems to be essential for a healthy body. Especially, the circulation down to the capillary blood vessel is very important. If a part of the body such as muscle causes pain, some of the capillary might be blocked by the swollen portion of pain such that the white blood corpuscles in blood may be hindered to reach the part of their need.

The present invention is configured to help the situation.

Accordingly, a need for a gemstone heating system has been present for a long time considering the expansive demands in the everyday life. This invention is directed to solve these problems and satisfy the long-felt need.

SUMMARY OF THE INVENTION

The present invention contrives to solve the disadvantages of the prior art.

An objective of the invention is to provide a gemstone heating system with magnet for expanding capillary vessel.

Another object of the invention is to provide a gemstone heating system with magnet for expanding capillary vessel, which helps pain relieving.

Still another object of the invention is to provide a gemstone heating system with magnet, which uses gemstone to spread out heat evenly over the pad.

An aspect of the invention provides a gemstone heating system for expanding capillary vessel.

The system comprises a gemstone heating pad, a magnet, a heat conductor, a heating element, and an insulating cover.

The gemstone heating pad comprises a front surface, a rear surface, a recess portion provided on a central portion of the rear surface, a enclosing wall portion configured for enclosing the recess portion.

The magnet is embedded in the recess portion of the gemstone heating pad.

The heat conductor encloses the recess portion of the gemstone heating system.

The heating element is disposed in the heating conductor.

The insulating cover is configured for insulating the heat conductor and the heating element.

The front surface of the gemstone heating pad may have a smoothly convex shape.

The gemstone heating pad may have a substantially circular disc shape.

The recess portion may be substantially circular. The gemstone heating pad may further comprise a groove for embedding the magnet. The groove may be located in a center of the recess portion.

The heat conductor may cover substantially whole area of the recess portion. The heating element may be located behind the magnet, and the heating element may overlap with the magnet when viewed from the front surface. The heating element may be powered electrically, and the heating element may be powered by a power supply provided separately. The power supply may comprise a plurality of batteries. The power supply may comprise a rechargeable battery.

The gemstone heating system may further comprise a handle. The gemstone heating pad may be disposed at an end of the handle, and the power supply may be disposed in the handle.

The gemstone heating system may further comprise: a heat controller disposed on a surface portion of the handle; a switch configured for turning on and off the power supply; and an optical indicator configured for indicating a plurality of operational status of the system.

The optical indicator may indicate temperature of the gemstone heating pad with color of light. The enclosing wall portion may be configured to engage the end of the handle through a mechanical fastener. The mechanical fastener may comprise a male thread provided on an outer surface of the enclosing wall portion, and the end of the handle may comprise a female thread corresponding to the male thread.

The insulating cover may be disposed over the recess portion of the gemstone heating pad, the heating conductor, and the heating element.

The advantages of the present invention are: (1) the gemstone heating system for expanding capillary vessel helps relieving pain from skin and tissues below; and (2) the gemstone heating system for expanding capillary vessel uses gemstone to facilitate blood circulation down to capillary.

Although the present invention is briefly summarized, the fuller understanding of the invention can be obtained by the following drawings, detailed description and appended claims.

BRIEF DESCRIPTION OF THE DRAWINGS

These and other features, aspects and advantages of the present invention will become better understood with reference to the accompanying drawings, wherein.

DETAILED DESCRIPTION EMBODIMENTS OF THE INVENTION

FIGS. 1-4 show a gemstone heating system 100 with magnet according to an embodiment of the present invention.

An aspect of the invention provides the gemstone heating system 100 with magnet for expanding capillary vessel.

Figure 3:
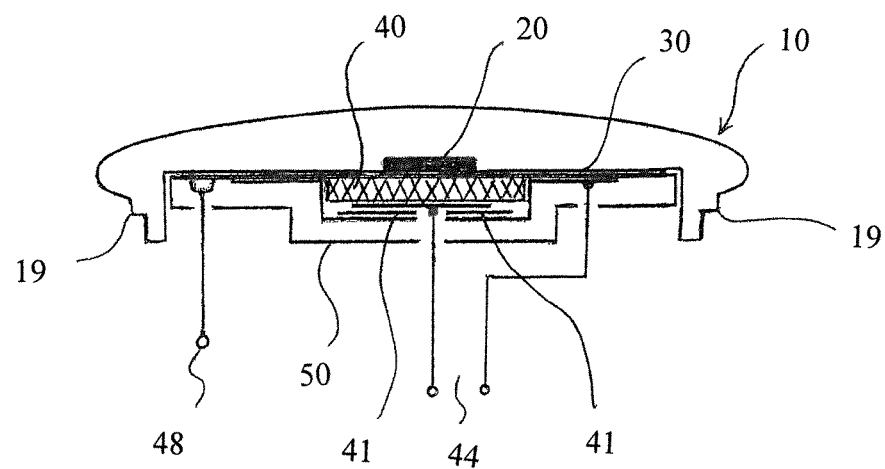
FIG. 3 is a cross-sectional view of a gemstone heating pad of a gemstone heating system assembled according to an embodiment of the invention.

The system comprises a gemstone heating pad 10, a magnet 20, a heat conductor 30, a heating element 40, and an insulating cover 50 as shown in FIG. 3.

The gemstone heating pad 10 comprises a front surface 12, a rear surface 14, a recess portion 16 provided on a central portion of the rear surface 14, a enclosing wall portion 18 configured for enclosing the rear surface 14, the recess portion 16.

The magnet 20 is embedded in the recess portion 16 of the gemstone heating pad 10.

The heat conductor 30 encloses the recess portion 16 of the gemstone heating system 100.

The heating element 40 is disposed in the heating conductor 30. The heating element 40 may be powered by a battery, which is going to be disclosed in detail below.

The insulating cover 50 is configured for insulating the heat conductor 30 and the heating element 40.

Figure 4:
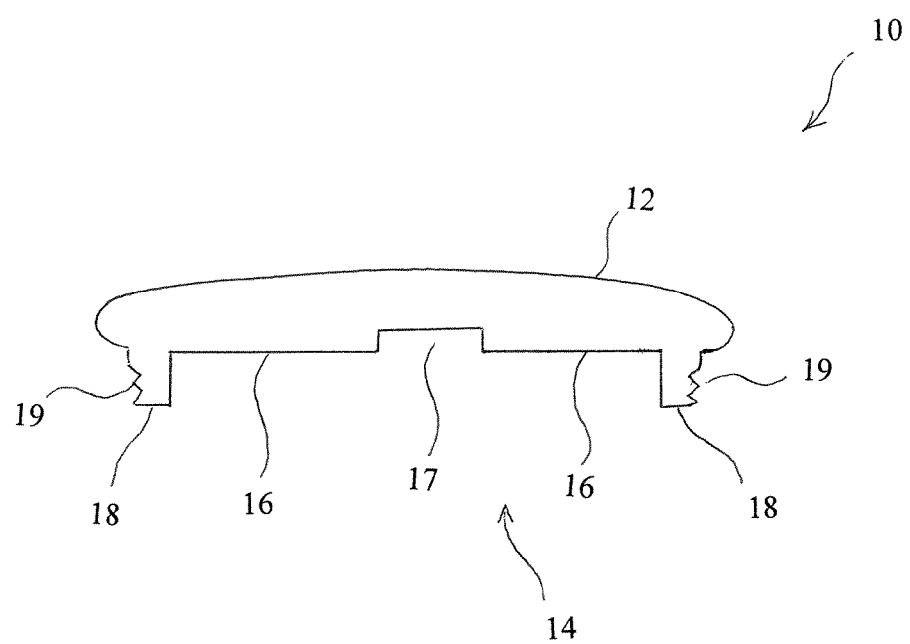
FIG. 4 is a cross-sectional view of a gemstone heating system according to another embodiment of the invention.

The front surface 12 of the gemstone heating pad 10 may have a smoothly convex shape as shown in FIGS. 3 and 4.

The gemstone heating pad 10 may have a substantially circular disc shape. However, the shape is not limited to the circular disc shape. As long as the front surface 12 is smooth enough, the overall shape of the gemstone heating pad 10 may be rectangular or even triangular.

The recess portion 16 may be substantially circular. The gemstone heating pad 10 may further comprise a groove 17 for embedding the, magnet 20. The groove 17 may be located in a center of the recess portion 16.

Figure 1:
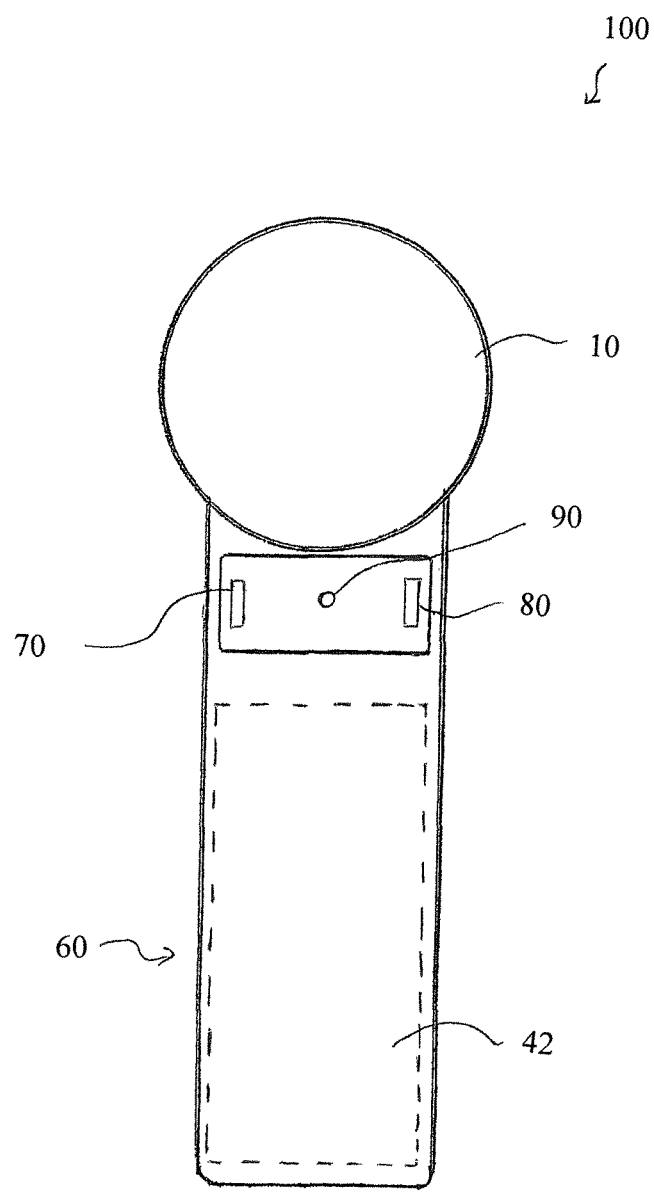
FIG. 1 is a front plan view showing a gemstone heating system according to an embodiment of the present invention.
Figure 2:
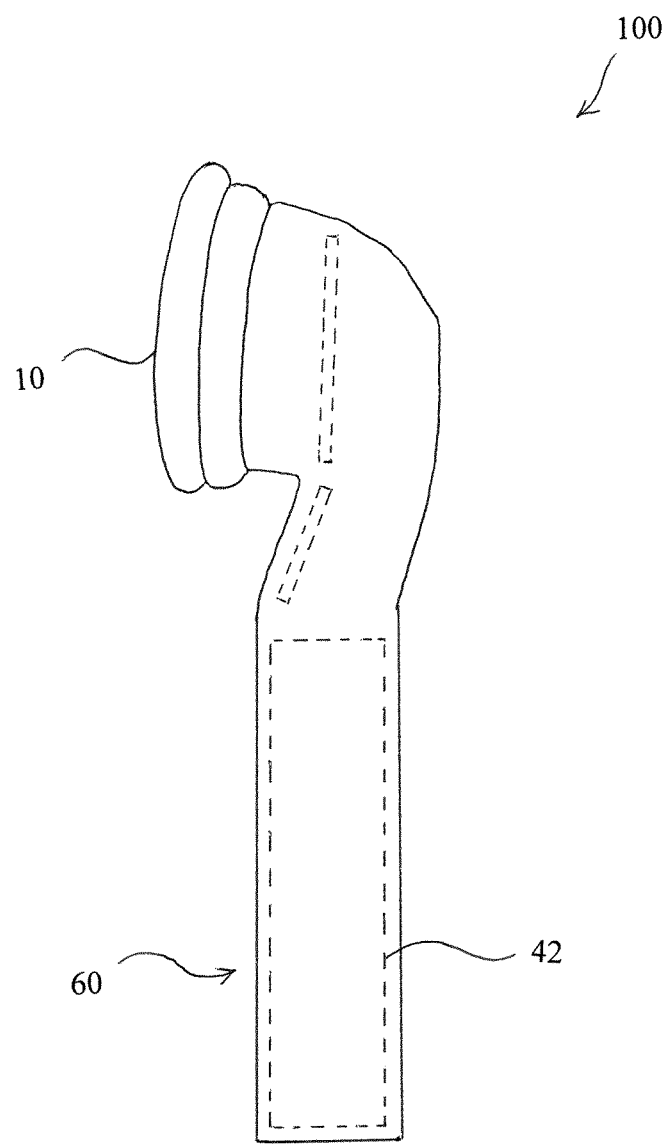
FIG. 2 is a side plan view of the gemstone heating system of FIG. 1.

The heat conductor 30 may cover substantially whole area of the recess portion 16. The heating element 40 may be located behind the magnet 20, and the heating element 40 may overlap with the magnet 20 when viewed from the front surface 12. The heating element 40 may be powered electrically, and the heating element 40 may be powered by a power supply 42 provided separately as shown in Figs. 1 and 2. The power supply 42 may comprise a plurality of batteries. The power supply 42 may comprise a rechargeable battery. The power supply 42 may be connected to the heating element 40 through wires 44 as shown in FIG. 3.

The gemstone heating system 100 may further comprise a handle 60. The gemstone heating pad 10 may be disposed at an end of the handle 60, and the power supply 42 may be disposed in the handle 60 as in FIGS. 1 and 2.

The gemstone heating system 100 may further comprise: a heat controller 70 disposed on a surface portion of the handle 60; a switch 80 configured for turning on and off the power supply 42; and an optical indicator 90 configured for indicating a plurality of operational status of the system 100.

The optical indicator 90 may indicate temperature of the gemstone heating pad 10 with color of light. The enclosing wall portion 18 may be configured to engage the end of the handle 60 through a mechanical fastener (not shown). The mechanical fastener may comprise a male thread 19 provided on an outer surface of the enclosing wall portion 18, and the end of the handle 60 may comprise a female thread corresponding to the male thread 19.

The insulating cover 50 may be disposed over the recess portion 16 of the gemstone heating pad 10, the heating conductor 30, and the heating element 40.

The gemstone heating pad 10 is effective to retain heat and release it to the tissue of a body through the skin in a comfortable feeling. Also, since the gemstone may be smoothened on the surface, the gemstone heating pad 10 may be very effective to caress the troubled portion of skin.

Once the gemstone heating system 100 makes contact with the troubled portion of the skin, the skin and the tissues below the skin are stimulated by the heat from the gemstone heating system 100, the muscle gets softer and the capillary blood vessel gets open to allow a plurality of white blood corpuscles gather around the spot, which will ease out the pain, and facilitates curing of the sore or muscle pain.

The thermal curing may be enhanced by the magnetic field from the magnet 20. It has been known that far infrared rays and negative ions are emitted from the gemstone, which will be helpful to relieve the pain.

The heating element 40 may be powered by DC 6-9V. The temperature range of the gemstone heating pad 10 may be from a room temperature to about 140 degrees in Celsius.

The method for using the gemstone heating system 100 may comprise steps of: switching the gemstone heating system 100 to obtain an appropriate temperature; pressing down the gemstone heating system 100 on a troubled portion of body for about 30 seconds to about a minute; and repeating the pressing step a plurality of times. The gemstone heating system 100 may be effective on the portions of neck, shoulder, legs, and stomach.

In certain embodiments of the invention, the heating pad 10 may comprise another material rather than a gemstone such as jade, agate, and plastic.

The gemstone heating system 100 produces the major effects by combining heat, gemstone, and magnet. The thermal energy from the heating pad 10 interacts with the gemstone. The magnetic energy from the magnet 20 works directly onto the tissues.

The magnet 20 is known to have some effect on the biological tissues, which might facilitate blood circulation or soften joints.

In FIG. 3, the heating conductor 30 may comprise a good thermal conductor including copper or silver. The heating element 40 may comprise material with high electrical resistivity such as Ni—Cr alloy, but not limited to it. The heating system 100 may further comprise another insulating layer 41 between two electrodes of the heating element 40 as shown in FIG. 3.

In certain embodiments of the invention, the heating system 100 may further comprise a temperature sensor 48. The temperature sensor 48 may be used to regulate the temperature of the heating element 40 through a thermostat device (not shown).

In other embodiments of the invention, the thermostat device may be disposed along the lead wires 44 close to the heating element 40.

While the invention has been shown and described with reference to different embodiments thereof, it will be appreciated by those skilled in the art that variations in form, detail, compositions and operation may be made without departing from the spirit and scope of the invention as defined by the accompanying claims.

What is claimed is:

1. A gemstone heating system with a magnet for expanding capillary vessels, the system comprising:
   a gemstone heating pad comprising a front surface, a rear surface, a recess portion provided on a central portion of the rear surface, an enclosing wall portion configured for enclosing the recess portion, wherein the gemstone heating pad is of a continuous surface that is unbroken and not ring-shaped;
   a magnet embedded in the recess portion of the gemstone heating pad;
   a heat conductor enclosing the recess portion of the gemstone heating system;
   a heating element disposed in the heating conductor, wherein the heating element is powered electrically, and wherein the heating element is configured to be powered by a power supply; and
   an insulating cover configured for insulating the heat conductor and the heating element so as to prevent the heat from propagating through the insulating cover,
   wherein the front surface of the gemstone heating pad is unbroken and blocks all the heat from behind the front surface, such that all the heat is delivered from the rear surface to the front surface through the gemstone heating pad,
   wherein the gemstone heating pad encloses the magnet, the heat conductor, the heating element, and the insulating cover from all directions except from behind the gemstone heating pad with the rear surface and the enclosing wall portion of the gemstone heating pad, wherein the magnet generates a magnetic field enhancing thermal curing of the gemstone heating system by facilitating blood circulation and softening joints, and wherein the heat generated by the heating element is delivered to the gemstone heating pad through the heat conductor, further comprising a handle, wherein the gemstone heating pad is disposed at an end of the handle, and wherein the power supply is disposed in the handle, and still further comprising:

a heat controller disposed on a surface portion of the handle;

a switch configured for turning on and off the power supply; and an optical indicator configured for indicating a plurality of operational status of the gemstone heating system.

2. The gemstone heating system of claim 1, wherein the front surface of the gemstone heating pad has a smoothly convex shape.

3. The gemstone heating system of claim 1, wherein the gemstone heating pad has a substantially circular disc shape.

4. The gemstone heating system of claim 1, wherein the recess portion is substantially circular.

5. The gemstone heating system of claim 4, wherein the gemstone heating pad further comprises a groove for embedding the magnet.

6. The gemstone heating system of claim 5, wherein the groove is located in a center of the recess portion.

7. The gemstone heating system of claim 1, wherein the heat conductor covers substantially the whole area of the recess portion.

8. The gemstone heating system of claim 7, wherein the heating element is located behind the magnet, and wherein the heating element overlaps with the magnet when viewed from the front surface.

9. The gemstone heating system of claim 1, wherein the power supply comprises a plurality of batteries.

10. The gemstone heating system of claim 1, wherein the power supply comprises a rechargeable battery.

11. The gemstone heating system of claim 1, wherein the optical indicator indicates a temperature of the gemstone heating pad with a color of light.

12. The gemstone heating system of claim 1, wherein the enclosing wall portion is configured to engage the end of the handle through a mechanical fastener.

13. The gemstone heating system of claim 12, wherein the mechanical fastener comprises a male thread provided on an outer surface of the enclosing wall portion, and wherein the end of the handle comprises a female thread.

14. The gemstone heating system of claim 1, wherein the insulating cover is disposed over the recess portion of the gemstone heating pad, the heating conductor, and the heating element.

15. A heating system with a magnet for expanding capillary vessels, the system comprising:

a heating pad comprising a front surface, a rear surface, a recess portion provided on a central portion of the rear surface, an enclosing wall portion configured for enclosing the recess portion, wherein the heating pad is of a continuous surface that is unbroken and not ring-shaped;

a magnet embedded in the recess portion of the heating pad;

a heat conductor enclosing the recess portion of the heating system;

a heating element disposed in the heating conductor, wherein the heating element is powered electrically, and wherein the heating element is configured to be powered by a power supply; and an insulating cover configured for insulating the heat conductor and the heating element so as to prevent the heat from propagating through the insulating cover, wherein the front surface of the heating pad is unbroken and blocks all the heat from behind the front surface, such that all the heat is delivered from the rear surface to the front surface through the heating pad, wherein the heating pad encloses the magnet, the heat conductor, the heating element, and the insulating cover from all directions except from behind the heating pad with the rear surface and the enclosing wall portion of the heating pad, and wherein the magnet generates a magnetic field enhancing thermal curing of the heating system by facilitating blood circulation and softening joints, wherein the heat generated by the heating element is delivered to the heating pad through the heat conductor, further comprising a handle, wherein the heating pad is disposed at an end of the handle, and wherein the power supply is disposed in the handle, and still further comprising:

a heat controller disposed on a surface portion of the handle;

a switch configured for turning on and off the power supply; and an optical indicator configured for indicating a plurality of operational status of the heating system.

16. The heating system of claim 15, wherein the front surface of the heating pad has a smoothly convex shape, wherein the heating pad has a substantially circular disc shape, wherein the recess portion is substantially circular, wherein the heating pad further comprises a groove for embedding the magnet, and wherein the groove is located in a center of the recess portion.

17. The heating system of claim 15, wherein the heating pad comprises one selected from a group consisting of gemstone, jade, agate, and plastic.

* * * * *